United States Patent [19]

Mawatari et al.

[11] Patent Number: 5,580,903
[45] Date of Patent: Dec. 3, 1996

[54] LIVER REGENERATION ACCELERATOR

[75] Inventors: Kazunori Mawatari; Katsumi Maezono, both of Kawasaki; Hiromitsu Arai, Tokyo; Toshio Maki, Kawasaki, all of Japan

[73] Assignee: Ajinomoto Co, Inc., Tokyo, Japan

[21] Appl. No.: 370,815

[22] Filed: Jan. 10, 1995

Related U.S. Application Data

[63] Continuation of Ser. No. 23,362, Feb. 26, 1993, abandoned.

[30] Foreign Application Priority Data

Feb. 26, 1992 [JP] Japan .................................. 4-039567

[51] Int. Cl.$^6$ ..................... A61K 31/205; A61K 31/195
[52] U.S. Cl. ....................... 514/556; 514/561; 514/563; 514/893; 514/894
[58] Field of Search ................................... 514/556, 561, 514/563, 893, 894

[56] References Cited

U.S. PATENT DOCUMENTS 4,987,123  1/1991  Masaki et al. ............................ 514/19

OTHER PUBLICATIONS

"Pharmacotherapy A Pathophysiologic Approach," DiPiro, J. T., et al., Elsevier, New York (1989) pp. 1600–1601 and 1639–1640.

Barber, J. R. et al. "Nutritional Support of Patients With Severe Hepatic Failure," Clinical Pharmacy, vol. 3 (1984) pp. 245–253.

*Primary Examiner*—Raymond Henley, III
*Assistant Examiner*—M. Moezie
*Attorney, Agent, or Firm*—Oblon, Spivak, McClelland, Maier & Neustadt, P.C.

[57] ABSTRACT

A method of treating a patient in need of stimulation of hepatocyte mitosis which comprises administering to said patient an effective amount of alanine and/or glutamine.

6 Claims, 5 Drawing Sheets

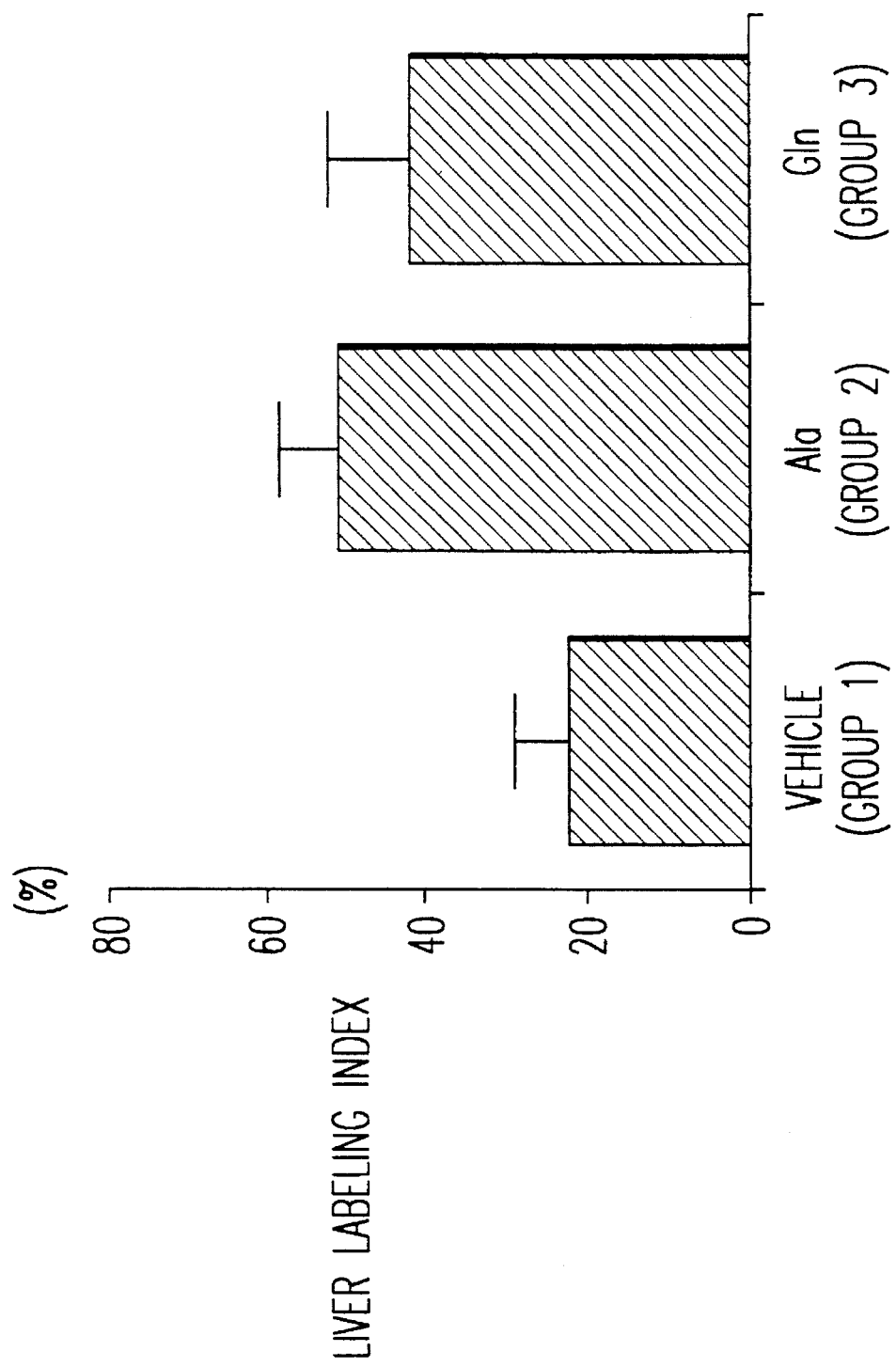

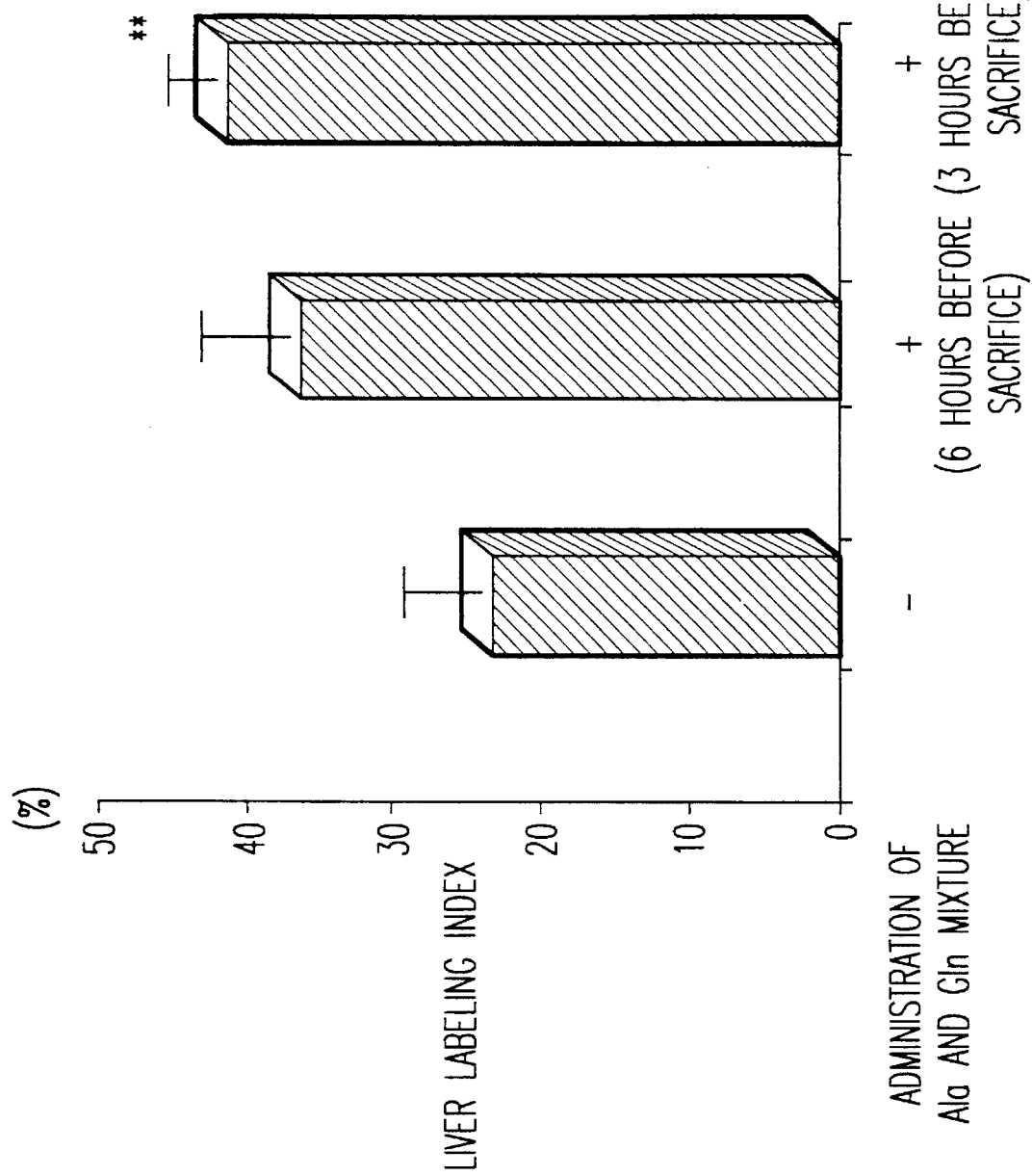

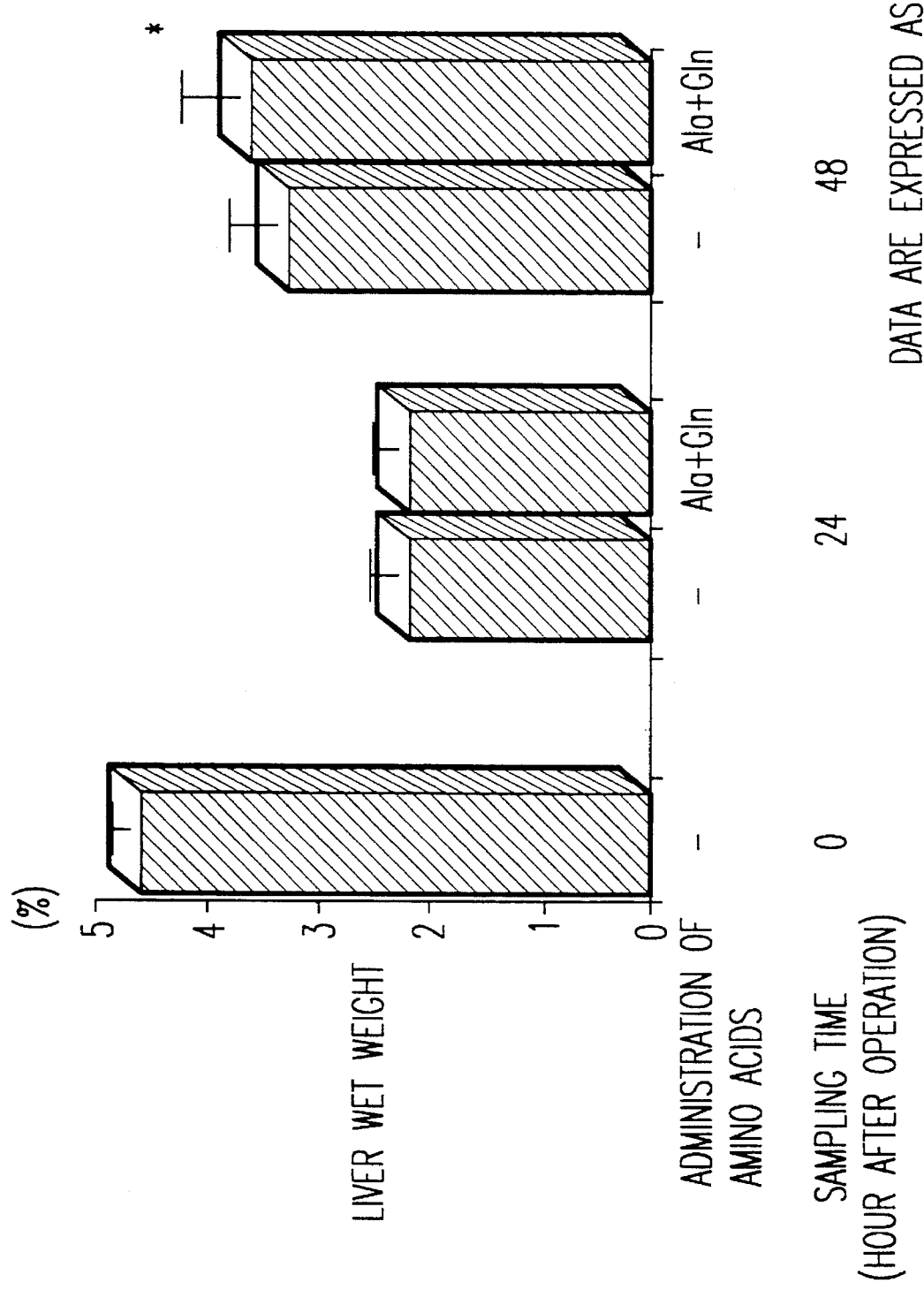

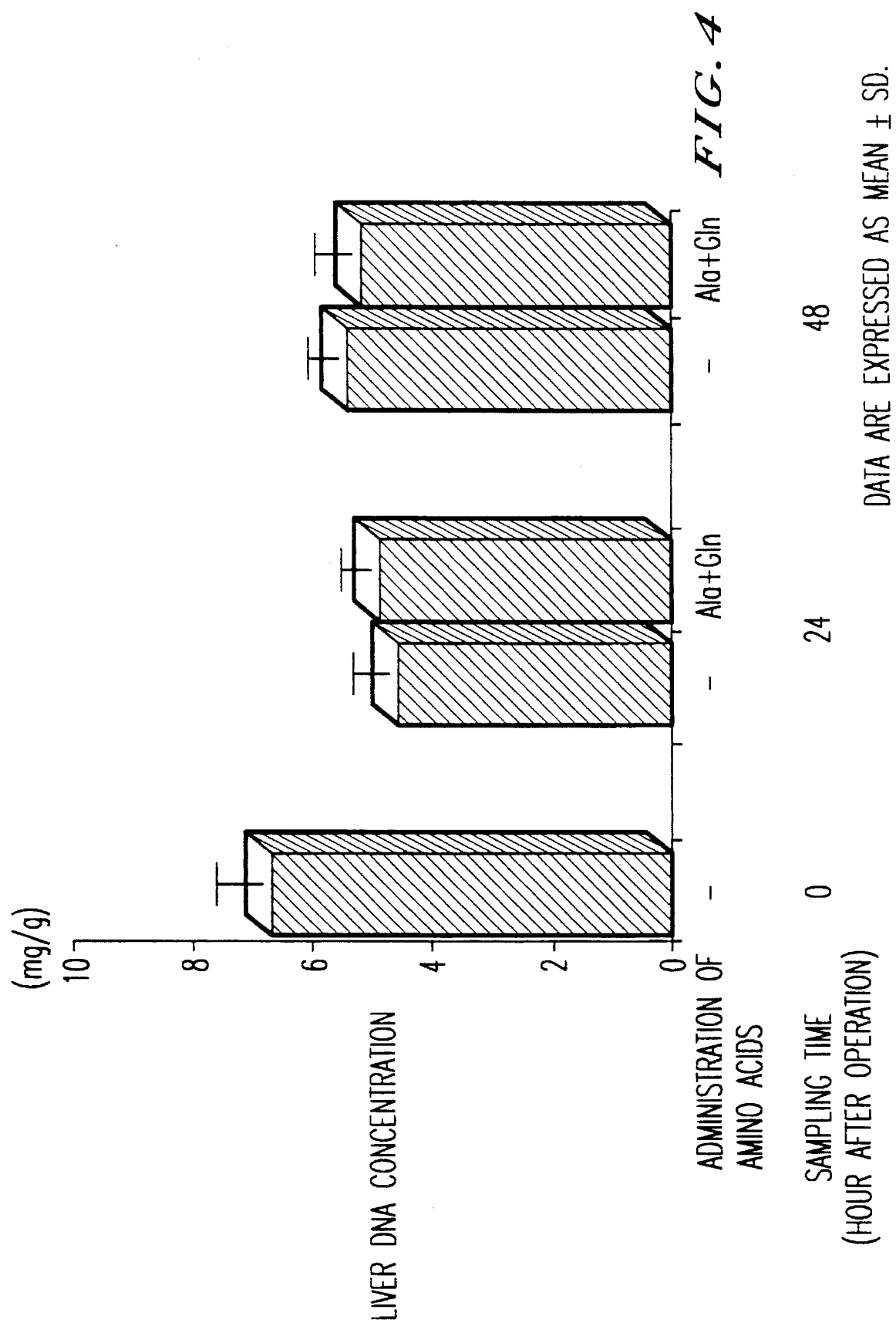

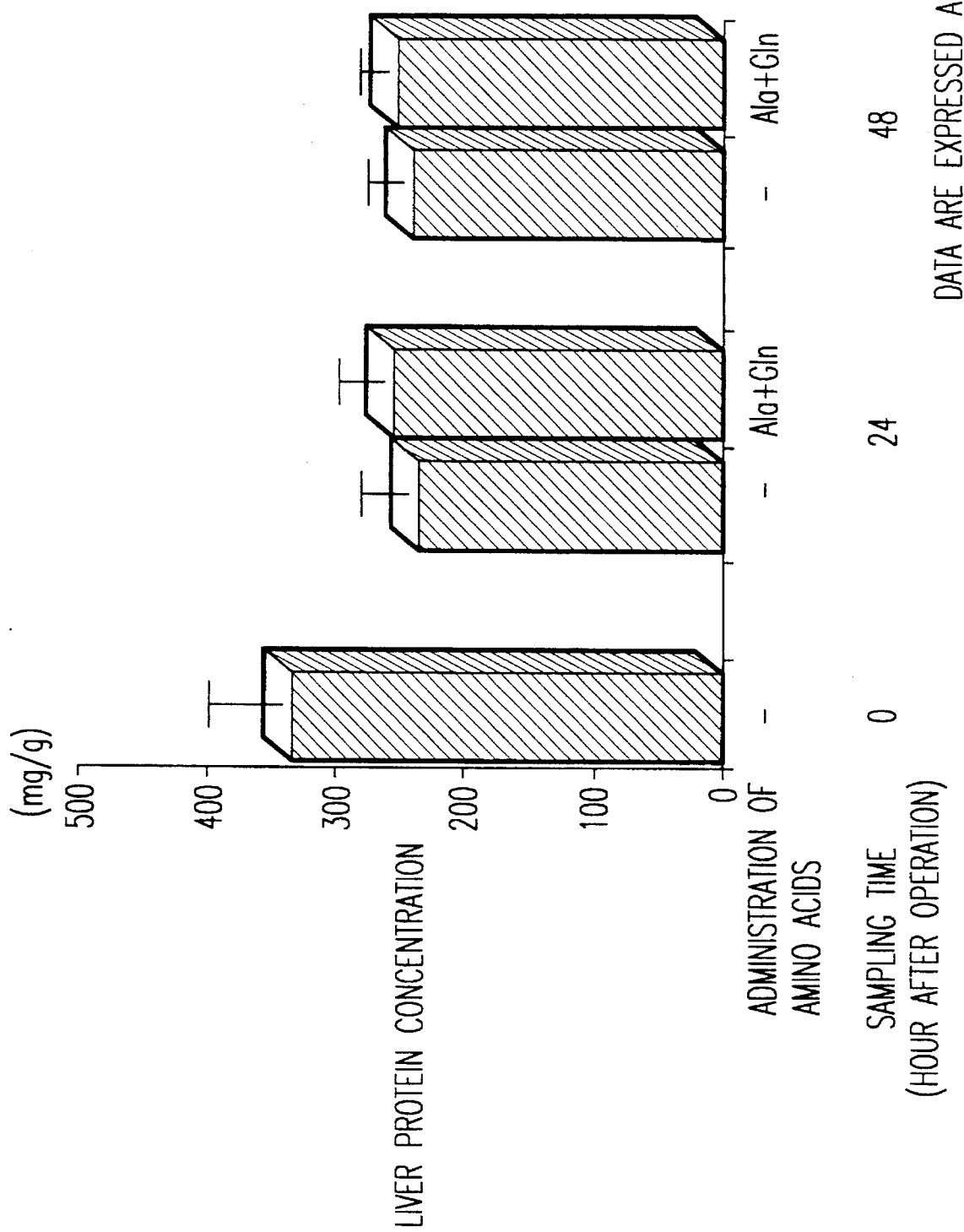

5,580,903

LIVER REGENERATION ACCELERATOR

This application is a continuation of application Ser. No. 08/023,362, filed on Feb. 26, 1993, abandoned.

BACKGROUND OF THE INVENTION

1. Field of the Invention

The present invention relates to a liver regeneration accelerator which is capable of causing an increase in hepatic cells to regenerate the liver.

2. Discussion of the Background

Fulminant hepatitis is the description of a condition involving sudden, widespread necrosis of hepatic cells due to causes such as the hepatitis virus, etc. Treatment of fulminant hepatitis includes interferon therapy, conventional anti-virus therapy, and the use of medicines which are generally used in the treatment of hepatitis. However, no direct effect on liver regeneration has been observed for interferon, while Glutathione and Tathion (Yamanouchi Seiyaku Co.) and Stronger Neo-Minophagen C (Minophagen Co.), which are generally used for hepatitis, improve the plasma transaminase value, but their effect on liver regeneration is limited.

Known therapeutic agents for liver damage serve to improve the function of liver tissue which has survived the initial cause of damage, however, the present goal is not simply to improve the condition of damaged tissue, but regeneration of liver cells by growth factors specific to hepatocytes. A known example of such an agent is hepatocyte growth factor (HGF), which stimulates the proliferation of cultured hepatocytes, and has an effect during cell division of hepatocytes, particularly during the G1 phase (DNA synthesis preinterphase) of the cell cycle. It is recognized as the major factor causing migration of hepatocytes to the S phase (DNA synthesis phase). This factor was expected to induce liver regeneration in the clinic as well. However, no improvement in the condition of patients with acute liver failure was observed despite high concentrations of HGF in the peripheral blood. Thus an awareness is growing of the necessity of participation of a factor other than HGF for liver regeneration, but so far no such factor capable of inducing liver regeneration in vivo to any significant degree has been discovered.

Masaki et al (U.S. Pat. No. 4,987,123) teaches that a composition comprising L-alanine and L-glutamine promotes ethanol clearance from blood and suppresses the serum enzymatic activities of glutamic oxaloacetic transaminase (GOT), glutamic pyruvic transaminase (GPT) and ornithine carbamyl transferase (OCT) which are symptoms associated with alcoholic hepatitis. It was found that alanine and glutamine could help restore liver function after ethanol loading.

Suda et al U.S. Pat. No. 4,596,825 teach a pharmaceutical composition for preventing or alleviating the effects of acute alcoholism, in particular liver disturbances in mammals, which comprises a mixture of alanine and ornithine. These compounds accelerate removal of ethanol and increase blood sugar and have a life saving affect in tests involving acute ethanol intoxication. Alleviation of disturbances in liver tissue was also noted.

The methods discussed above are known to reduce the incidence of swollen liver cells and improve the overall function of remaining liver tissue. However, no factor capable of inducing liver regeneration was described.

The present invention aims to provide an effective liver regeneration accelerator which is capable of causing an increase in hepatic cells to accelerate liver regeneration after liver tissue has been destroyed by disease or surgical procedures. In addition, the present invention is useful in liver transplantation procedures.

SUMMARY OF THE INVENTION

An object of the present invention is to provide a method of treating a patient in need of stimulation of hepatocyte mitosis which comprises administering to said patient an effective amount of alanine and/or glutamine.

BRIEF DESCRIPTION OF THE DRAWINGS

FIG. 1: Stimulatory effect of alanine and glutamine mixture administration on rat liver labeling index in experiment 1.

FIG. 2: Stimulatory effect of alanine and glutamine mixture administration on rat liver labeling index in experiment 2.

FIG. 3: Effect of alanine and glutamine mixture administration on the change of rat liver wet weight after partial hepatectomy during experiment 3.

FIG. 4: Change of rat liver DNA concentration in experiment 3. Administration of alanine and glutamine mixture was performed at every 6 hours after the hepatectomy.

FIG. 5: Change of rat liver protein concentration in experiment 3. Administration of alanine and glutamine mixture was performed at every 6 hours after hepatectomy.

DETAILED DESCRIPTION OF THE PREFERRED EMBODIMENT

We have administered alanine, glutamine and mixtures thereof to rats whose livers were partially removed, as a representative evaluation system for liver regeneration, and found that the liver labeling index, a liver regeneration indication, rose while the liver wet weight increased. This increase in liver wet weight was not accompanied by any difference between hepatectomized group in hepatic DNA or protein concentration, but was due to the increase in hepatocytes, and is therefore a result of acceleration of liver regeneration. Thus, it was discovered that alanine and glutamine used separately or in admixture function to accelerate regeneration of the liver and thereby increase liver weight.

In other words, a liver regeneration accelerator according to the present invention contains an effective amount of alanine and/or glutamine as a necessary ingredient. When the amino acids alanine and glutamine are used in admixture, they may be combined in an arbitrary manner, but are preferably combined at a ratio of 1/0.1–1/10 by weight more preferably 1/0.5–1/5. The two amino acids may be used as a dipeptide or tripeptide when they are used in combination.

A liver regeneration accelerator according to the present invention may be used in the form of, for example, powder, granules, tablets, sugar-coated tablets, capsules, a liquid preparation, etc. for oral administration, or for example, a suspension, emulsion, ampule, injection, etc. for parenteral administration, or in the form of a combination thereof. The injection may be in the form of an amino acid infusion, and may be made as a preparation containing either or both of alanine and glutamine at a proportion of 12% or more by weight of the total amount of the total amino acids, or at a daily dosage of 10 g or more of the two.

The dosage may be easily determined depending on the symptoms observed, but should be a dosage of 1–20 g or more per day for adults of either alanine or glutamine or a mixture thereof. Also, in order to ascertain the effect of liver regeneration acceleration, administration should be effected continually at intervals of, for example, 3 hours or 6 hours. Alanine and glutamine have each been approved as foods, and there is hence no possibility of toxicity, and particularly, acute toxicity.

Therefore, alanine, glutamine and mixtures thereof accelerate liver regeneration and are useful for the general improvement of liver damage involving destruction of liver tissue. The present invention provides a therapeutic agent for fulminant hepatitis, as a remedial agent for viral hepatitis, and as a therapy or prophylactic agent against hepatopathy caused by drugs such as anti-cancer agents, etc. In addition, it may be expected to have a wide variety of applications similar to those of HGF for the acceleration of liver regeneration following operations for liver transplantation, etc., and for the inducement of kidney regeneration.

Other features of the invention will become apparent from the following examples which are given for illustration of the invention and not intended to be limiting thereof.

Experiment 1

Partial hepatectomy (68% hepatectomy) was performed for male Sprague-Dawley rats weighing 120–140 g according to the methods of Higgins and Anderson (Higgins GM, Anderson RM:Experimental pathology of the liver, 1, Restoration of the white rats following partial surgical removal. Arch. Pathol. 12:186–202, 1931), and rats were killed 24 hours after the operation. Three hours before the sacrifice, alanine (group 2) or glutamine (group 3) were administered to rats orally (22.45 mmol/kg body weight). Animals in control group (group 1) were not administered amino acids but vehicle. Specimens from each rat liver were prepared and stained with anti-PCNA (Proliferating Cell Nuclear Antigen) antibody. The mitotic activity was determined by counting the number of parenchymal cells undergoing mitosis according to the methods of Tanaka et al (in "Byori to rinsyo", 9.(6):791–798, 1991) and the labeling index was calculated.

|  | Partial hepatectomy | Administration of amino acids | n |
| --- | --- | --- | --- |
| Group 1 | + | — | 10 |
| Group 2 | + | Ala (3 hours before sacrifice) | 10 |
| Group 3 | + | Gln (3 hours before sacrifice) | 10 |

FIG. 1 shows the result of this experiment. In rat liver from group 2 and 3, higher mitotic activity were observed than in liver from group 1. So, both alanine and glutamine are effective on stimulation of hepatocyte's mitotic activity.

Experiment 2

Partial hepatectomy was performed for male SD rats weighing 120–130 g according to the methods of Higgins and Anderson, and they were killed 24 hours after the operation. Three or 6 hours before the sacrifice, alanine and glutamine mixture (alanine weight and glutamine weight were in the ratio of 1:1) was administered to rats orally (2 g/kg body weight).

Animals in control group (group 1) were not administered amino acids but vehicle. One hour before the killing, bromodeoxyuridine was administered to all rats by intraperitoneal injection (40 mg/kg body weight) and liver labeling index was determined according to the methods of Sanuki et al (in "Kanzo", 27.(11):1632, 1986).

|  | Partial hepatectomy | Administration of amino acids | n |
| --- | --- | --- | --- |
| Group 1 | + | — | 6 |
| Group 2 | + | Ala + Gln (6 hours before sacrifice) | 8 |
| Group 3 | + | Ala + Gln (3 hours before sacrifice) | 8 |

FIG. 2 shows the result of this experiment. In the case that alanine and glutamine mixture was administered to rats 3 hours before killing (group 3), liver labeling index was much higher than control group (group 1). A significant difference was observed between group 3 and group 1 at the 99% confidence coefficient. In group 2 (alanine and glutamine mixture was administered to rats 6 hours before sacrifice), a much higher labeling index than control group were observed in 5 out of 8 rats. All rats received food ad libitum after the operation to 3 hours before killing. Each rat's food intake was about 9 g and there was no correlation between food intake and the labeling index in control group.

Experiment 3

Partial hepatectomy was performed for male SD rats weighing 140–180 g according to the methods of Higgins and Anderson. On the other hand, 6 rats were sham-operated as an intact control group. An alanine and glutamine mixture (weight ratio of 1:1) was administered to rats orally (1 g/kg body weight, group 3 and group 5) at 6, 12, 18, 24, 30, 36 and 42 hours after the hepatectomy. Some animals (group 2, group 4) were given no amino acids administration. At 24 hours (group 2, group 3) and 48 hours (group 4, group 5 and group 1) after the operation, liver wet weight, liver DNA concentration and liver protein concentration were measured. Furthermore, histological examination was performed.

|  | Partial hepatectomy | Administration of amino acids | Sampling time (Hour after operation) | n |
| --- | --- | --- | --- | --- |
| Group 1 | — | — | 48 | 6 |
| Group 2 | + | — | 24 | 11 |
| Group 3 | + | Ala + Gln | 24 | 11 |
| Group 4 | + | — | 48 | 11 |
| Group 5 | + | Ala + Gln | 48 | 11 |

FIG. 3 shows the changes of liver wet weight after partial hepatectomy. Liver weights of animals administered alanine and glutamine were much higher than those of rats not administered amino acids. Significant differences in liver weights were observed between the administered group and non-administered group at 48 hours after the operation (confidence coefficient=99%).

The DNA concentration and protein concentration in liver was not significantly different between groups which were administered amino acids compared with groups that were not administered amino acids, so it is clear that the increase of liver weight observed in alanine and glutamine treated groups depended on the increase of hepatocyte number. These results show clearly that administration of alanine, glutamine and mixtures thereof is effective for stimulation of liver regeneration.

Obviously, numerous modifications of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for treating viral hepatitis consisting essentially of:

administering an effective amount of alanine and glutamine to a patent having viral hepatitis.

2. The method of claim 1 wherein the amount of alanine is 1–20 g/day and the amount of glutamine is 1–20 g/day.

3. The method of claim 1 wherein the ratio of alanine to glutamine is 1/0.1–1/10.

4. A method for treating a partial hepatectomy patient consisting essentially of:

a) performing a partial hepatectomy on a subject in need thereof, b) administering alanine and glutamine to said subject in an amount effective to stimulate liver regeneration.

5. The method of claim 4 wherein the amount of alanine is 1–20 g/day and the amount of glutamine is 1–20 g/day.

6. The method of claim 4 wherein the ratio of alanine to glutamine is 1/0.1–1/10.

* * * * *

UNITED STATES PATENT AND TRADEMARK OFFICE
CERTIFICATE OF CORRECTION

PATENT NO. : 5,580,903

DATED : December 3, 1996

INVENTOR(S) : Kazunori MAWATARI, et al.

It is certified that error appears in the above-identified patent and that said Letters Patent is hereby corrected as shown below:

Column 5, line 6, "a patent having" should read
--a patient having--.

Signed and Sealed this

Twenty-fourth Day of March, 1998

Attest:

BRUCE LEHMAN

Attesting Officer

Commissioner of Patents and Trademarks